US008511822B2

(12) United States Patent
Buehren

(10) Patent No.: US 8,511,822 B2
(45) Date of Patent: Aug. 20, 2013

(54) METHODS FOR THE TRANSFORMATION OF MEASURED VALUES OF A CHARACTERISTIC OF THE CORNEA AND APPARATUS FOR THE MEASUREMENT OF THE TOPOGRAPHY OF THE CORNEA

(75) Inventor: Tobias Buehren, Magdala (DE)

(73) Assignee: Carl Zeiss Meditec AG, Jena (DE)

( * ) Notice: Subject to any disclaimer, the term of this patent is extended or adjusted under 35 U.S.C. 154(b) by 381 days.

(21) Appl. No.: 12/818,256

(22) Filed: Jun. 18, 2010

(65) Prior Publication Data

US 2010/0321483 A1    Dec. 23, 2010

(30) Foreign Application Priority Data

Jun. 19, 2009   (DE) .................. 10 2009 030 154

(51) Int. Cl.
*A61B 3/14*       (2006.01)
*A61B 3/10*       (2006.01)

(52) U.S. Cl.
USPC .......................................... 351/206; 351/212

(58) Field of Classification Search
USPC .................................................. 351/206, 212
See application file for complete search history.

(56) References Cited

U.S. PATENT DOCUMENTS

| 5,850,531 | A | 12/1998 | Cox et al. |
|---|---|---|---|
| 6,213,605 | B1 | 4/2001 | D'Souza et al. |
| 6,257,723 | B1 | 7/2001 | Sarver et al. |
| 6,382,794 | B1 | 5/2002 | Lai et al. |
| 6,529,900 | B1 | 3/2003 | Patterson et al. |
| 2002/0198516 | A1 | 12/2002 | Knopp et al. |
| 2004/0059321 | A1 | 3/2004 | Knopp et al. |
| 2008/0100612 | A1 | 5/2008 | Dastmalchi et al. |
| 2009/0160859 | A1* | 6/2009 | Horowitz et al. ............. 345/440 |

FOREIGN PATENT DOCUMENTS

DE    10 2007 052 282    5/2009

OTHER PUBLICATIONS

Tobias Buehren et al., "The Stability of Corneal Topography in the Post-Blink Interval", Contact Lens and Visual Optics Laboratory, Center for Eye Research, School of Optometry, Queensland University of Technology Brisbane, Australia; 2001 Lippincott Williams & Wilkins, Inc., Philadelphia; Cornea vol. No. 8, 2001.

Tobias Buehren et al., "Corneal Aberrations and Reading", Contact Lens and Visual Optics Laboratory, Center for Eye Research, School of Optometry, Queensland University of Technology Brisbane, Australia; Optometry and Vision Science, vol. 80, No. 2, Feb. 2003.

* cited by examiner

*Primary Examiner* — Mahidere Sahle
(74) *Attorney, Agent, or Firm* — Frommer Lawrence & Haug LLP

(57) ABSTRACT

A method for the transformation of measured values of a characteristic of the cornea and apparatus for measuring the topography of the cornea. The method involves using a parameterized assignment rule, providing a slider as an operating control, determining a current setting of the slider, and determining a parameter of the assignment rule based on the determined setting of the slider. The observer can sift through a large number of variants of the assignment rule within a short time without prior knowledge by means of the slider to extract information at different parameter settings in an economical manner.

14 Claims, 2 Drawing Sheets

METHODS FOR THE TRANSFORMATION OF MEASURED VALUES OF A CHARACTERISTIC OF THE CORNEA AND APPARATUS FOR THE MEASUREMENT OF THE TOPOGRAPHY OF THE CORNEA

The present application claims priority from German Patent Application No. DE 10 2009 030 154.2 filed on Jun. 19, 2009, the disclosure of which is incorporated herein by reference in its entirety.

BACKGROUND OF THE INVENTION

1. Field of the Invention

The invention is directed to methods for the transformation of local measured values of a characteristic of a cornea, particularly an optical characteristic of a cornea, or values derived therefrom in a false color image according to an assignment rule for unambiguous mapping of a first range of values, or range of values, to a set of false colors and apparatus for implementing a method of this kind, particularly apparatus for measuring the topography of a cornea, having a light source for structured illumination, a camera, a display, and a control unit which is connected to the camera and to the display and which is designed to record an image of the cornea by means of the camera for determining local measured values of a characteristic of the cornea, particularly an optical characteristic of the cornea, or values derived therefrom based on the image and for displaying the model on the display in a false color scale according to an assignment rule for the unambiguous mapping of a first range of values to a set of false colors.

2. Description of Related Art

A high-resolution profile of the cornea which determines particularly its imaging characteristics or surface characteristics can be achieved by measuring the topography of the cornea of the human eye (photokeratoscopy or videokeratography), which is known per se. The corneal profile can be used for diagnosing, planning surgical procedures on the cornea, and for adjusting eyeglasses or contact lenses. Typically, a Placido ring projector which projects concentric rings on the cornea is used to determine corneal topography. By imaging reflections of the rings, an optical characteristic of the reflecting surface (i.e., of the cornea) can be determined based on the resulting deformation in the reflected image. For example, heights or local refractive powers (or the corresponding radii of curvature) of the cornea can be measured in this way. Methods for determining corneal topography based on Placido ring projection are described, for example, in U.S. Pat. Nos. 6,213,605, 6,382,794, or 6,257,723.

In the prior art, the measured values recorded at different locations of the cornea are graphically displayed as plane projections in false colors (color coding), which is known as a topography map. In so doing, a fixed range of values is divided into steps (subintervals), each of which is displayed unambiguously by an element of a given set of false colors, for example, color interval(s) or discrete colors. By varying a color component, for example, the hue, saturation or intensity, intermediate steps can be generated. Generally, a standardized assignment rule is used for color coding, for example, based on ANSI Z80.23-2008 or ISO 19980:2005. Images of different patients or of the same patient at different points in time can be compared to one another visually using a standardized color coding which distributes the possible hues over the refractive powers (or radii of curvature) usually occurring at the human eye.

However, owing to the limited quantity of available hues and the limited capability of the human eye to resolve degrees of brightness, this kind of graphic display has the disadvantage that, depending on the range of values, either only local variations of low amplitude around an identical, or at least similar, base value or only an overview of the total topography in which local variations of low amplitude are suppressed can be perceived. Further, it is impossible to show local variations of low amplitude around two (or more) distinctly different base values in a visually perceptible manner. It is known to determine a deviant assignment rule manually in order to observe a determined range of values in a manner specific to the eye, for example; however, this requires expert knowledge owing to the complexity of the possible variants and is time-consuming even for experts.

SUMMARY OF THE INVENTION

Therefore, it is the object of the invention to provide improved methods and apparatus of the type mentioned above which makes it possible to visually extract a greater amount of information from a false color display in an economical manner.

This object is met by a method having the features indicated in claim 1 and by apparatus having the features indicated in claim 10 or 11.

Advantageous embodiments of the invention are indicated in the subclaims.

According to the invention, a parameterized assignment rule is used, a slider is provided as an operating control, a current setting of the slider is determined, and a parameter of the assignment rule is determined based on the determined setting of the slider, or the assignment rule is parameterized, and the apparatus has a slider by means of which a parameter of the assignment rule can be adjusted.

A parameterized assignment rule for mapping measured values to false colors can comprise one or more parameterized transfer functions (for example, one per color component R/G/B or H/S/V or H/L/S of the false colors) or a plurality of look-up tables (LUT). For example, the range of values to be displayed is mapped by a parameterized transfer function to the hue component H (hue) of digital color values in an HSV or HLS color space, particularly to a true subset of the technically possible values of component H, wherein the two remaining components are kept constant. With a given set of false colors, possible parameters of a parameterized transfer function of this kind are a boundary or a central value of the range of values to be mapped (at a given width of the value range) or both boundaries of the range of values to be mapped (so that the width of the range of values is variable). The quantity of steps (or step width) is given by the quantity of colors contained in the given false color set which is fixed for every given color interval in digital color display. When look-up tables are used as an assignment rule, the parameterization can be used for the selection of a look-up table (or of a set of look-up tables for a plurality of color components).

A slider is a one-dimensionally variable adjusting control so that exactly one parameter of a parameterized assignment rule can be adjusted by means of the slider. The user (observer) can sift through a large number of variants of the assignment rule within a short time without prior knowledge by means of a slider to extract information at different parameter settings in an economical manner.

In so doing, a width of the range of values to be mapped is preferably specified and a lower limit, a central value, or an upper limit of the first range of values is determined as a parameter based on the setting of the slider. In other words, a lower limit, a central value, or an upper limit can be adjusted as a parameter of the assignment rule by means of the slider. For example, peculiarities of the corneal topography which are manifested by slight local variations of the measured characteristic can be determined by using a correspondingly small width of the range of values to be mapped. The false color transformation then acts as a virtual loupe which magnifies a section of the cornea and can be moved quickly over the cornea by means of the slider. Accordingly, it is possible to visually perceive local variations of small amplitude around two (or more) distinctly different base values quasi-simultaneously.

In addition, the assignment rule advantageously maps a second range of values adjoining the first range of values to a second set of false colors disjunct from the first set, wherein a ratio of a width of the second range of values to a quantity of false colors in the second set is greater than a ratio of the width of the first range of values to a quantity of false colors in the first set. The transformation then comprises a spread of the total given false color scale in a sub-range of the measured values and in a portion of the false color image, wherein the absolute position of the color-spread sub-range can be adjusted by means of the slider. Based on the rougher ratio of values to colors, the resolution of the color scale is worse outside the virtual loupe (outside the first range of values) than if the false colors were evenly distributed over both ranges. However, the relationship of the magnified region(s) to the rest of the topography can be visually perceived better than when (as a possible alternative) exclusively the first range of values is mapped in the false color image. The values of the second range are preferably smaller than those of the first range and, in a corresponding manner, a third range whose values are greater than those of the first range of values is mapped to a third mutually disjunctive false color set. An assignment rule determined analytically can advantageously be continued in the second range and possibly additional ranges taking into account the reduced color resolution.

A switch is advantageously provided for switching between use of the parameterized first assignment rule for the transformation and use of a second assignment rule for the transformation. In a corresponding manner, the apparatus is provided with a switch for switching the display between the parameterized first assignment rule and a second assignment rule. This makes it possible to search for local variations in a false color loupe in an economical manner, wherein it is possible to change to a (e.g., standardized) overview color scale or another color scale with minimal effort. To this end, the entire width of the range of values of the first assignment rule which are to be mapped and the (individual) range of values of the second assignment rule to be mapped is preferably adjusted corresponding to the values of the measured characteristic which (usually) occur at the human eye or corresponding to the extent of the actually existing measured values (or of the values derived therefrom).

In particularly preferred embodiments, the slider is used as the switch in that switching to the use of the parameterized first assignment rule is identified by a user based on touching the slider and switching to the use of the second assignment rule is identified by the user by letting go of the slider. To this end, the slider can comprise the switch in such a way that switching to the use of the parameterized assignment rule can be initiated by a user by touching the slider and switching to the use of the second assignment rule can be initiated by the user by letting go of the slider. This simplifies operation because the virtual loupe can be switched on and moved by the same action, which corresponds to the actuation of a real loupe.

An assignment rule which is not dependent on the parameter of the parameterized assignment rule that can be determined based on the slider is preferably used as a second assignment rule. This allows orientation of the user to a constant scale, particularly to a known (standard) scale.

The current setting of the slider and the parameter of the assignment rule are advisably repeatedly determined based on the current setting or, alternatively, a setting-changing process of the slider is determined and the current setting and the parameter of the assignment rule are then determined based on the current setting. This makes it possible for the user to change the parameter continuously.

Height, local radius of curvature, or local refractive power is typically measured as a characteristic of a cornea.

In preferred embodiment forms, a respective set of measured values is recorded multiple times at given locations on the cornea and at least one of the quantities comprising mean value, standard deviation and quantity of valid measurements is determined for each location as a derived value and is transformed, particularly by determining and displaying locations at which the determined quantity exhibits a significant change between sequences. Accordingly, the slider makes it possible to detect slight changes between measurements of the same eye at different points in time. In particular, the invention makes it possible to differentiate between genuine changes and systematic measurement errors (errors of accuracy) or statistical measurement inaccuracies (errors of precision) in that a difference map is generated from the mean values, standard deviations and quantities of valid measured values at every location, which difference map represents the locations with significant changes. The repeated measurement at different times, including such evaluation of statistical quantities, is known, for example, from Buehren, Collins, Carney, "Corneal aberrations and reading", *Optometry and Vision Science* 80, 159-166, whose disclosure is incorporated herein as far as possible.

An apparatus according to the invention can advantageously be outfitted with a first operating control which initiates storage of the parameter on a storage medium and with a second operating control which initiates reproduction of the parameter from the storage medium. Accordingly, an individually adjusted color coding can be repeated and, in particular, applied to sequential measurements of the same cornea and difference maps resulting therefrom. In this way, even very small changes can be visualized by color. In an advantageous manner, the operating controls can be those for storing and reproducing the measured values and/or the values derived therefrom. To the extent that the set of false colors which is to be used (and, therefore, the step sizes of the transformation) can be adjusted by the user, these data are likewise advisably stored and reproduced.

The invention also comprises control units and computer programs which are designed to implement a method according to the invention. For example, a control unit or a computer program can comprise the following software modules:

a software module for providing a software slider as operating control or a software module for polling a hardware slider, particularly after an interrupt request (IRQ), a software module for determining a current setting of the slider, a software module for determining a parameter of the assignment rule based on the determined setting of the slider, wherein the software module uses a parameterized assignment rule.

This can be the same software module in each case when it meets all of the requirements listed above or can be a plurality of separate software modules, each of which meets one or more of the above-mentioned requirements.

BRIEF DESCRIPTION OF THE DRAWINGS

Corresponding parts have identical reference numbers in both drawings.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 1:
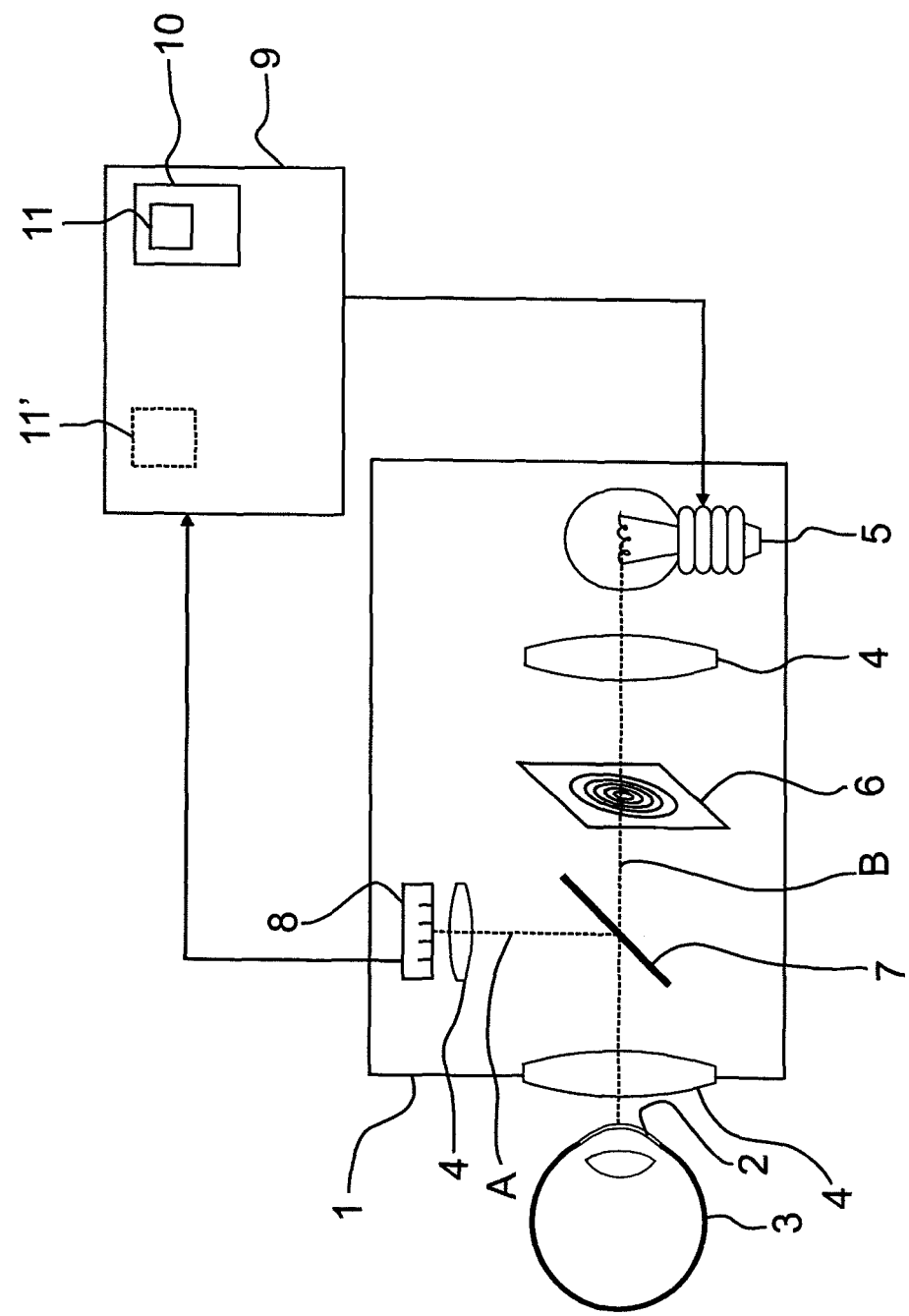
FIG. 1 shows a schematic view of an apparatus for measuring the topography of a cornea.

FIG. 1 shows schematically an apparatus 1 for measuring the topography of a cornea 2 of an eye 3 which can be used separately or, in particular, in an ophthalmic device (not shown), for example, a videokeratograph. In the latter case, the imaging beam path A of the arrangement 1 can be part of the imaging beam path of the ophthalmic device. The arrangement 1 has optical elements 4 in the illumination beam path B for projecting a pattern diaphragm 6 on the cornea 2, which pattern diaphragm 6 is illuminated by a light source 5 and has, for example, 26 Placido rings. The imaging beam path A is reflected into the illumination beam path B by a beamsplitter 7 and contains an optical element 4 and a spatially resolving camera 8 for imaging and recording the cornea 2 which is illuminated in a structured manner by the Placido rings.

The control unit 9 is connected to the camera 8 for image recording and to the light source 5 for illumination control and comprises a display 10. The control unit 1 has a slider 11 in the display 10 as an operating control for software. Alternatively, the slider 11' can be arranged at the control unit 9 itself or at another location of the apparatus 1 as a physical operating control.

In a measuring pass, local axial radii of curvature, for example, are determined at 128 locations per Placido ring (i.e., a total of 3328 measured values). The measured values occupy, for example, a range of values from 31.0 to 64.0 D (diopters).

Figure 2:
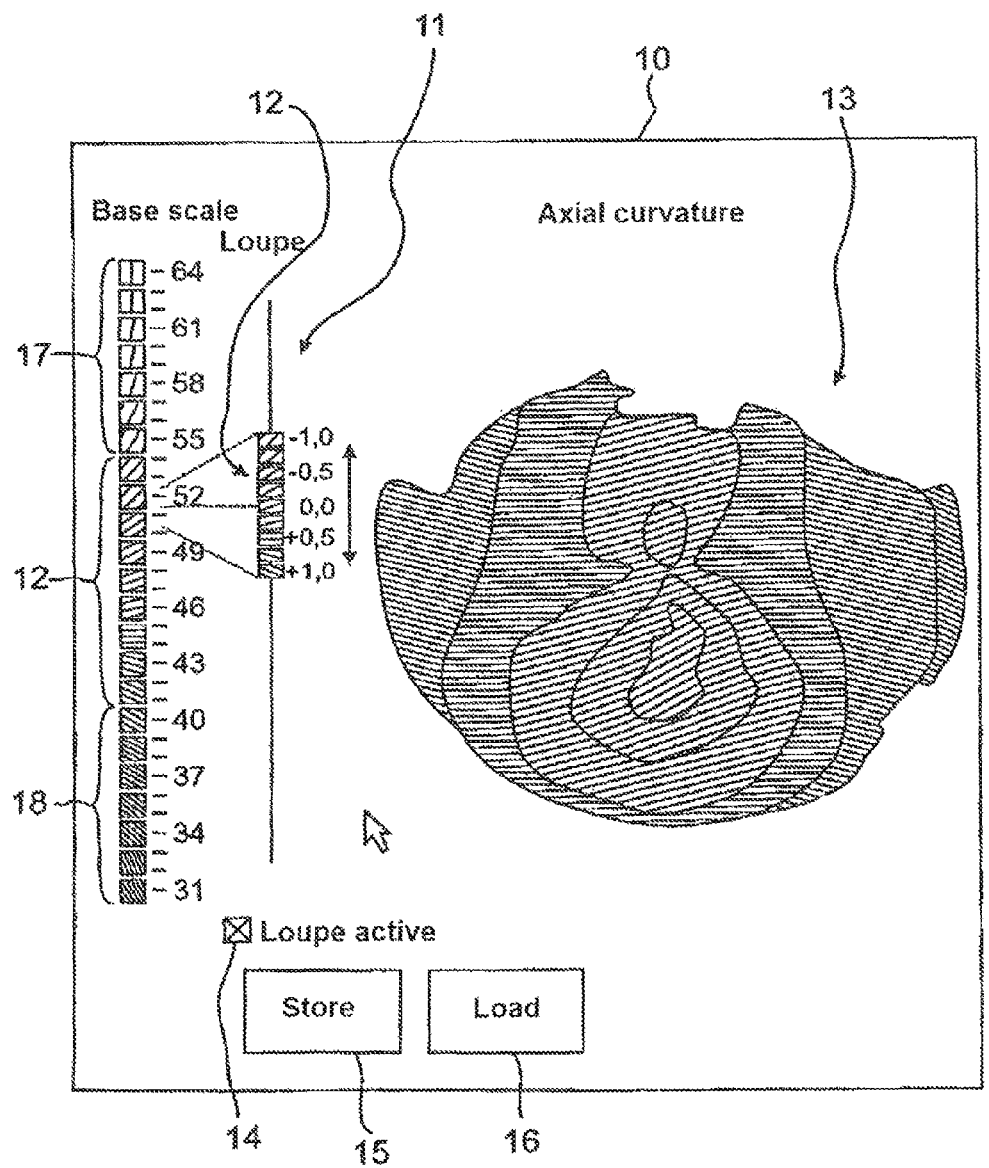
FIG. 2 shows a schematic view of a display of the control unit of the apparatus.

FIG. 2 shows, by way of example, a display 10 of the control unit 9. After the evaluation of the recorded image and derivation of local measured values for an optical characteristic (e.g., the local axial radii of curvature of the cornea described above), a topography map is displayed on the display 10 as a false color image 13 after transformation of the measured values. The transformation is carried out by the control unit 9. There is a supply of, for example, 23 false colors with different hues, indicated by different hatching, for the transformation. The supply is divided into a first set 12, a second set 17, and a third set 18 of false colors. One of two different assignment rules of measured values to false colors is used in the transformation. The first assignment rule is, for example, a parameterized transfer function which maps a first value range of fixed width (in the example, deviations of −1 to +1 corresponding to a width of two), which is adjustable by means of a parameter, to the first set 12 of false colors which comprises, for example, nine false colors, wherein the fixed width can be changed in a configuration module of the control unit 9 by a user. The adjustable parameter indicates, for example, the central value of the first range of values which corresponds to a deviation from zero and, therefore, from the mean value of the nine loupe false colors. A second range of values, whose amount lies below the first range of values, is mapped in the second false color set 17. A third range of values which lies above the first range of values in amount is mapped in the third false color set 18. The boundaries of the range of values are adjustable by means of the parameter. A finer color resolution results in the first range of values due to the fact that the first range of values is appreciably narrower than the other two ranges. The second assignment rule is another transfer function in which the specified range of values to be mapped (in the example, 31 to 64 corresponding to a width of 33) is uniformly distributed to the false color sets 12, 17, 28 so that the generated false color image 12 is a (constant) overview topography map of the cornea 2 with average color resolution. The specified range of values of the second assignment rule can likewise be changed in a configuration module of the control unit 9 by the user so that other color scales can be adjusted.

The slider 11 serves as a false color loupe which can be activated by means of a switch 14 instead of the overview topography map. The first assignment rule is used for generating the false color image 13 when the false color loupe is activated in the transformation, wherein the parameter of the transfer function which indicates the central value in the example is determined based on the slider position. The slider 11 can be touched by a mouse cursor M and a mouse button (not shown) by moving the cursor M over the grip of the slider 11 and pressing the mouse button. The slider can be displaced by moving the cursor M while holding down the mouse button so that the parameter of the transfer function can be adjusted.

Accordingly, in the mapped current recording in which the false color loupe is activated, the first range of values from 50.4 to 52.4 (loupe range) is mapped to the new false colors of the first set 12, the second range of values from 52.4 to 64.4 is mapped to the seven false colors of the second set 17, and the third range of values from 30.6 to 50.4 is mapped to the seven false colors of the third set 18. Accordingly, there is a color resolution of about 0.22 D per false color in the loupe range, and, outside the loupe range, about 2.83 D per false color in the second range of values and about 1.71 D per false color in the third range of values. Alternatively, it is possible to switch to the transformation for the overview map by means of the switch 14. In the overview map, for example, all of the measured values from 30.6 to 64.4 are mapped uniformly to the 23 false colors; i.e., there is a color resolution of about 1.47 D per false color. The color scale of the loupe is spread out in the loupe range compared to the color scale of the overview map and is compressed outside the first range of values compared to the color scale of the overview map. Therefore, the topography of the cornea with locally increased resolution can be extracted from the false color map in an unambiguous manner. In this example, the color resolution in the second and third range of values changes dynamically depending on the slider position because the false colors 12 used for the first range of values are constant. In alternative embodiment forms (not shown), the false colors 12 for the first range of values can be given dynamically (for example, selected automatically from a given total set, wherein the rest of the colors are used for the other sets 17, 18) so that the difference in color resolution between the second range of values and the third range of values is reduced (preferably minimized). In this case, the set 12 of false colors is advisably selected contiguously.

In alternative embodiment forms (not shown), the grip of the slider 11 (i.e., the slider 11 itself) serves as a switch for switching between the overview and the false color loupe. As soon as the cursor M is located over the handle of the slider 11 and the mouse button is pressed, the false color image 13 is generated and displayed by means of the first assignment rule. When the mouse button is not pressed (or is released), the false color image 13 is generated and displayed by means of the second assignment rule as an overview topography map.

In all of the embodiment forms, clicking the mouse on a location of the overview topography map, which is equivalent to clicking on a position of the slider 11 which moves the slider 11 to this position, can be identified with activation of the false color loupe, wherein the slider position and the transfer function parameter (central value of the deviation interval) are set to a value of the displayed cornea characteristic corresponding to this location.

Further, the control unit 9 has a software button as operating control 15 in the display 10 for storing the parameter adjusted at the slider 11 on a storage medium, for example, a hard drive or network storage, and a software button as third operating control 16 for reproducing the parameter from the storage medium.

In all of the embodiment forms, the set 12 of false colors and the subset used for the false color loupe can be adjusted by the user in a configuration module of the control unit 9.

The invention can advantageously be used in particular in connection with an analysis and display of significant changes in a cornea over time according to FIG. 5 in Buehren, Collins, Carney, "Corneal aberrations and reading", *Optometry and Vision Science* 80, 159-166. A respective slider is then provided as a false color loupe for each part of FIG. 5. This can be carried out, for example, in a combination device for topographic measurement and ocular wavefront measurement.

However, the method according to the invention is preferably implemented independently from apparatus for measuring, for example, by a control unit such as a personal computer (PC) in a doctor's office, the measurement being carried out, for example, by an optometrist who transfers the measured values to the doctor's office by means of an electronic medium.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

Reference Numbers 1 apparatus for measuring the topography of a cornea
2 cornea
3 eye
4 optical element
5 light source
6 pattern diaphragm
7 beamsplitter
8 camera
9 control unit
10 display
11 slider
12 first set of false colors
13 false color image
14 switch
15 first operating control
16 second operating control
17 second set of false colors
18 third set of false colors
A imaging beam path
B illumination beam path
M cursor

What is claimed is:

1. A method comprising:
transforming local measured values of a characteristic of a cornea or values derived therefrom in a false color image according to an assignment rule for unambiguous mapping of a first range of values to a set of false colors;
wherein a parameterized assignment rule is used;
wherein a slider is provided as an operating control;
wherein a current setting of the slider is determined;
wherein a parameter of the assignment rule is determined based on the determined setting of the slider;
wherein the assignment rule additionally maps a second range of values adjoining the first range of values to a second set of false colors disjunct from the first set; and
wherein a ratio of a width of the second range of values to a quantity of false colors in the second set is greater than a ratio of the width of the first range of values to a quantity of false colors in the first set.

2. The method according to claim 1;
wherein a width of the range of values to be mapped is specified; and
wherein a lower limit, a central value, or an upper limit of the range of values is determined as a parameter of the assignment rule based on the setting of the slider.

3. The method according to claim 1;
wherein a switch is provided for switching between use of the :parameterized assignment rule for the transformation and use of a second assignment rule for the transformation.

4. The method according to claim 3,
wherein the slider is used as the switch; and
wherein switching to the use of the parameterized first assignment rule is identified by a user based on touching the slider, and switching to the use of the second assignment rule is identified by the user by letting go of the slider.

5. The method according to claim 3;
wherein an assignment rule which is not dependent on the parameter of the parameterized first assignment rule that can he determined based on the slider is used as second assignment rule.

6. The method according to claim 1;
wherein the current setting of the slider and the parameter of the assignment rule are repeatedly determined based on the current setting; or
wherein a setting changing process of the slider is determined and the current setting and the parameter of the assignment rule are then determined based on the current setting.

7. The method according to claim 1;
wherein height, local radius of curvature, or local refractive power is measured as a characteristic of a cornea.

8. The method according to claim 1;
wherein a respective set of measured values is recorded multiple times at given locations at the cornea; and wherein at least one of mean value, standard deviation, and quantity of valid measurements is determined for each location as a derived value and is transformed by determining and displaying locations at which the determined quantity exhibits a significant change between sequences.

9. A Control unit or computer program designed to implement the method according to claim 1.

10. An apparatus for measuring the topography of a cornea, comprising:
- a light source for structured illumination;
- a camera;
- a display; and
- a control unit which is connected to the camera and to the display;
- wherein the control unit is designed to record an image of the cornea by means of the camera for determining local measured values of a characteristic of the cornea or values derived therefrom based on the image and for displaying the model on the display in a false color scale according to an assignment: rule for the unambiguous mapping of a first range of values to a set of false colors,
- wherein the assignment rule is parameterized;
- wherein the apparatus has a slider by means of which a parameter of the assignment rule can be adjusted; and
- wherein the control unit is constructed according to the method of claim 1.

11. The apparatus according to claim 10, further comprising:
- a switch for switching We display between the parameterized assignment rule and a second assignment rule.

12. The apparatus according to claim 11;
- wherein a lower limit., a central value, or an upper limit can be adjusted by means of the slider as a parameter of the assignment rule.

13. The apparatus according to claim 11;
- wherein the slider is used as a switch, so that switching to the use of the parameterized first assignment rule can be initiated by a user by touching the slider, and switching to the use of the second assignment rule can be initiated by the user by letting go of the slider.

14. The apparatus according to claim 9, further comprising
- a second operating control which initiates a storage of the parameter on a storage medium; and
- a third operating control which initiates a reproduction of the parameter from the storage medium.

* * * * *